United States Patent
Lede et al.

(10) Patent No.: US 6,383,477 B1
(45) Date of Patent: May 7, 2002

(54) VOLUME-IMPARTING HAIR TREATMENT COMPOSITIONS

(75) Inventors: Michael Lede, Langen; Susanne Birkel, Glashuetten; Michael Franzke, Rossdorf; Hildegard Henze, Darmstadt, all of (DE)

(73) Assignee: Wella Aktiengesellschaft, Darmstadt (DE)

(*) Notice: Subject to any disclaimer, the term of this patent is extended or adjusted under 35 U.S.C. 154(b) by 0 days.

(21) Appl. No.: 09/629,954

(22) Filed: Aug. 1, 2000

(30) Foreign Application Priority Data

Aug. 7, 1999 (DE) .......................................... 199 37 386

(51) Int. Cl.⁷ ............................ A61K 7/06; A61K 7/11; A61K 7/00
(52) U.S. Cl. ..................... 424/70.15; 424/47; 424/70.1; 424/70.11; 424/70.12; 424/70.14; 424/70.27; 424/70.28
(58) Field of Search ................. 424/401, 70.1, 424/70.11, 70.12, 47, 70.15, 70.14, 70.27, 70.28

(56) References Cited

U.S. PATENT DOCUMENTS 5,626,836 A * 5/1997 Liu et al.
6,207,778 B1 * 3/2001 Jachowicz et al.

FOREIGN PATENT DOCUMENTS

| DE | 44 01 708 A1 | 7/1995 |
|----|--------------|--------|
| DE | 196 42 622 A1 | 4/1998 |
| DE | 198 05 434 A1 | 8/1999 |
| EP | 0 074 191 A2 | 3/1983 |
| EP | 0 524 346 A1 | 1/1993 |
| EP | 0 535 429 A2 | 7/1993 |
| FR | 2 403 076 | 9/1977 |
| WO | 95/00104 | 1/1995 |
| WO | 96/06592 | 3/1996 |
| WO | 96/19971 | 7/1996 |

OTHER PUBLICATIONS

Computer Printout from the Company STN File CBNB, AN 14 (17): 24036, (1998).
Volumen Kommt und Bleibt! In Business Report 19, Feb. 2001.

* cited by examiner

Primary Examiner—Gollamudi S. Kishore
Assistant Examiner—Brian K. Seidleck
(74) Attorney, Agent, or Firm—Michael J. Striker

(57) ABSTRACT

The hair treatment compositions for imparting volume to hair each contain from 0.1 to 20 percent by weight of one or more terpolymers of vinyl pyrrolidone, vinyl caprolactam and a basic acryl amide monomer and from 0.05 to 10 percent by weight of one or more cation-active hair-care substance. The composition provides a long-lasting volumizing effect to hair treated with it. It is especially effective on damaged hair and provides good combability without loading the hair.

12 Claims, No Drawings

VOLUME-IMPARTING HAIR TREATMENT COMPOSITIONS

BACKGROUND OF THE INVENTION

1. Field of the Invention

The subject matter of the present invention is a hair treatment composition containing a terpolymer of vinyl pyrrolidone, vinyl caprolactam and a basic acrylamide monomer and an additional cation-active hair-care material.

2. Prior Art

Hair treatment compositions, which impart volume and hold to the hair, are known. The cosmetic polymers normally used for this purpose have good fixing properties in aqueous or alcoholic solutions, which shape and fix the hair more or less well after application and can also impart more volume to the hair. However frequently this effect does not last long and the desired volume imparting effect is already partially lost by combing the hair thoroughly. The hair style already collapses in a few hours especially with fine hair, i.e. the volume effect does not last over an entire day from morning to evening. Many of the fixing or volume imparting polymers have frequently undesirable side effects, which are made noticeable because the treated hair feels rough, has too high a load or insufficient elasticity or too much visible residue builds up on the hair.

Terpolymers of vinyl pyrrolidone, vinyl caprolactam and 3-(N-dimethylaminopropyl)methacrylamide are known from WO 96/19971. The use of these polymers in fixing compositions, especially in aerosol and pump sprays, is also known. These polymers are especially suitable for use in aqueous spray formulations with a reduced content of readily volatile organic ingredients (low VOC sprays). The polymers have good fixing properties, but impart a relatively rough feel to the hair and produce a comparatively high load on the hair.

SUMMARY OF THE INVENTION

It is an object of the present invention to provide a hair treatment composition that has the advantages of a typical styling composition, and especially is characterized by a long-lasting volumizing effect, while at the same time it guarantees good hair care properties, especially in regard to elasticity, reduced load and reduced residue on the hair.

It is also an object of the present invention to provide a hair treatment composition with ingredients, which are compatible with each other, i.e. the composition should be homogeneous, clear and unintended precipitation of ingredients should be avoided.

It has now been found that these objects are attained by a hair treatment composition comprising (A) at least one terpolymer of vinyl pyrrolidone, vinyl caprolactam and a basic acrylamide monomer, and (B) at least one hair-care material with at least one cationic group.

The terpolymer (A) is contained in the composition according to the invention preferably in an amount of from 0.01 to 20, especially preferably from 0.1 to 5, percent by weight, and the cationic hair-care material is contained in an amount of from 0.01 to 10 percent by weight, especially preferably from 0.05 to 5 percent by weight.

DETAILED DESCRIPTION OF THE INVENTION

Suitable terpolymers (A) include those in which the acrylamide monomer is selected from the group consisting of dialkylaminoalkylmethacrylamides having alkyl group containing one to four carbon atoms and dialkylaminoalkylacrylamides having alkyl group containing one to four carbon atoms. Dimethylaminopropylmethacrylamide is especially preferred. A method of making a polymer of this type is described in WO 96/19971. This polymer can be obtained commercially under the trademark AQUAFLEX® SF 40 (ISP).

The cationic material (B) is a substance, which has a substantive action on human hair because of its cationic or cationizable groups, especially primary, secondary, tertiary or quaternary amine groups. Suitable cation-active substances are selected from the group consisting of cationic surfactants, amphoteric betainic surfactants, cationic polymers, silicone compounds with cationic or cationizable groups, cationic derivatized proteins or protein hydrolyzates and betaine.

Suitable cation-active surfactants are surfactants which contain a quaternary ammonium groups. Cation-active surfactants include cationic or amphoteric betainic surfactants. Suitable cationic surfactants contain amino groups or quaternarized hydrophilic ammonium groups, which carry a positive charge in solution and can be represented by the general formula I:

$$N^{(+)}R^1R^2R^3R^4X^{(-)} \qquad (I),$$

wherein $R^1$ to $R^4$ each represent, independently of each other, an aliphatic group, an aromatic group, an alkoxy group, a polyoxyalkylene group, an alkylamido group, a hydroxyalkyl group, an aryl group or an alkaryl group, each with 1 to 22 carbon atoms, and $X^{(-)}$ represents an anion, especially halogen, acetate, phosphate, nitrate or alkylsulfate, preferably chloride. The aliphatic groups can also have cross-linkages or other groups such as amino groups.

For example, the following are suitable cationic surfactants: the chlorides or bromides of alkyidimethylbenzyl ammonium salts, alkyltrimethyl ammonium salts, especially cetyltrimethyl ammonium chloride or cetyltrimethyl ammonium bromide, tetradecyltrimethyl ammonium chloride or tetradecyltrimethyl ammonium bromide, alkyldimethylhydroxyethyl ammonium chloride or alkyldimethylhydroxyethyl bromide, dialkyldimethyl ammonium chloride or dialkyldimethyl ammonium bromide, alkylpyridinium salts, especially laurylpyridinium chloride or cetylpyridinium chloride, alkylamidoethyl trimethyl ammonium ether sulfate and compounds with cationic character, such as amine oxides, especially alkylmethylamine oxide or alkylaminoethyldimethylamino oxide. Cetyltrimethyl ammonium chloride is particularly preferred, for example in the form of a 26 percent aqueous solution marketed under the trademark DEHYQUART® A of Hinkel KGaA, Düsseldorf, Germany; and under the trademark GENAMIN® CTAC of Hoechst AG, Frankfurt, Germany and in the form of a 50 percent solution in isopropanol under the trademark ARQUAD® 16–50 of Akzo Chemicals GmbH, Düren, Germany.

Suitable amphoteric surfactants are derivatives of aliphatic quaternary ammonium, phosphonium and sulfonium compounds of formula (II):

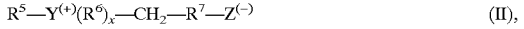

$$R^5-Y^{(+)}(R^6)_x-CH_2-R^7-Z^{(-)} \qquad (II),$$

wherein $R^5$ is a straight chain or branched alkyl-, alkenyl- or a hydroxyalkyl group with 8 to 18 carbon atoms and from 0 to about 10 ethylene oxide units and 0 to 1 glyceryl unit; Y represents an N-, P- or S-containing group; $R^6$ represents an alkyl or monohydroxyalkyl group with one to three carbon atoms; X is equal to one in case that Y is a sulfur atom and X is equal to 2 in case Y is a nitrogen or a phosphorous atom; $R^7$ is an alkylene or hydroxy-alkylene group with one to four carbon atoms and $Z^{(-)}$ represents a carboxylate, sulfate, phosphonate or phosphate group.

Other amphoteric surfactants, such as betaines, are similar suitable for the composition according to the invention. These betaines include, for example, $C_8$- to $C_{18}$-alkylbetaines, such as cocodimethylcarboxymethylbetaine, lauryldimethylcarboxymethylbetaine, lauryldimethylalphacarboxyethylbetaine, cetyldimethylcarboxymethylbetaine, oleyldimethylgammacarboxypropylbetaine and lauryl-bis-(2-hydroxypropyl) alphacarboxyethylbetaine; $C_8$- to $C_{18}$-sulfobetaines, such as cocodimethylsulfopropylbetaine, stearyldimethylsulfopropylbetaine, lauryldimethylsulfoethylbetaine, lauryl-bis-(2-hydroxyethyl)sulfopropylbetaine; carboxyl derivatives of imidazoles, $C_8$- to $C_{18}$-alkyldimethyl ammonium acetate, $C_8$- to $C_{18}$-alkyldimethylcarbonylmethyl ammonium salts and $C_8$- to $C_{18}$-fatty acid alkylamido betaines, such as coconut oil fatty acid amidopropylbetaine, which is marketed in the form of a 30% aqueous solution under the trademark TEGO® Betaine L7 of Goldschmidt AG and N-coconut oil fatty acid amidoethyl-N-[2-(carboxymethoxy)ethyl]-glycerol (CFTA name: cocoamphocarboxyglycinate), which is marketed, for example, in the form of a 50% aqueous solution under the trademark MIRANOL® C2M of Miranol Chemical Co. Inc.

The suitable cation-active polymers are preferably hair-fixing or hair-conditioning polymers. Suitable polymers of ingredient (B) contain preferably quaternary amine groups. The cationic polymers can be homopolymers or copolymers, in which the quaternary nitrogen groups either are contained in polymer chains or backbones or preferably as substituents in one or more of the monomers. Monomers containing ammonium groups monomers can be copolymerized with non-cationic monomers. Suitable cationic monomers include unsaturated, radically polymerizable compounds, which have at least one cationic group, especially ammonium-substituted vinyl monomers, such as trialkylmethacryloxyalkyl ammonium groups, trialkylacryloxyalkyl ammonium groups, dialkyldiallyl ammonium groups and quaternary vinyl ammonium monomers with cyclic, cationic nitrogen-containing groups, such as pyridinium, imidazolium or quaternary pyrrolidones, e.g. alkylvinyl imidazolium, alkylvinylpyridinium, or alkylvinylpyrrolidone salts. The alkyl groups of these monomers are preferably lower alkyl groups, such as $C_1$- to $C_7$-alkyl groups, especially preferably $C_1$- to $C_3$-alkyl groups.

The monomers containing the ammonium groups can be copolymerized with non-cationic monomers. Suitable comonomers are, for example, acrylamide, methacrylamide, alkylacrylamides, dialkylacrylamides, alkylmethacrylamides, dialkylmethacrylamides, alkylacrylates, alkylmethacrylates, vinyl caprolactone, vinylcaprolactam, vinyl pyrrolidone, vinyl esters, e.g. vinyl acetate, vinyl alcohols, propylene glycol or ethylene glycol. The alkyl groups of these monomers are preferably $C_1$- to $C_7$-alkyl groups, especially preferably $C_1$- to $C_3$-alkyl groups.

Suitable polymers with quaternary amino groups are, for example, the polymers described in the CTFA Cosmetic Ingredient Dictionary under the trade name, polyquaternium, for example methylvinylimidazolium chloride/vinyl pyrrolidone copolymer (polyquaternium-16) or quaternized vinyl pyrrolidone/ dimethylaminoethylmethacrylate copolymer (polyquaternium-11) and quaternary silicone polymers or oligomers, such as silicone polymers with quaternary terminal groups (quaternium-80).

For example, vinylpyrrolidone/dimethylaminoethylmethacrylate methosulfate copolymer, which is sold under the trademarks GAFQUAT® 755N and GAFQUAT® 734 of GAF Co., USA, is especially suitable as the cationic polymer in the composition according to the invention. GAFQUAT® 734 of GAF Co., USA, is especially preferred. Additional cationic polymers, are, for example, the copolymer of polyvinyl pyrrolidone and imidazolimine methochloride, marketed under the trademark LUVIQUAT® HM 550 of BASF, Germany; the terpolymer of dimethyldiallyl ammonium chloride, sodium acrylate and acrylamide sold under the trademark MERQUAT® Plus 3300 by Calgon, USA; the terpolymer of vinyl pyrrolidone, dimethylaminoethylmethacrylate and vinyl caprolactam marketed under the trademark GAFFIX® VC 713 of ISP, USA; and vinyl pyrrolidone/methacrylamidopropyltrimethyl ammonium chloride copolymer marketed under the trademark GAFQUAT® HS 100 of GAF Inc.

Suitable cationic polymers, which are derived from natural polymers, are cationic derivatives of cellulose, starch or guar. Chitosan and chitosan derivative compounds are suitable. Cationic polysaccharides have the general formula (III):

$$G\text{—}O\text{—}B\text{—}N^+R^aR^bR^cX^{(-)} \qquad (III),$$

wherein

G is a anhydroglucose residue, for example starch or cellulose anhydroglucose;

B is a divalent group, for example, an alkylene, an oxyalkylene, a polyoxyalkylene or hydroxyalkylene;

$R^a$, $R^b$ and $R^c$ are each, independently of each other, alkyl, aryl, alkylaryl, arylalkyl, alkoxyalkyl or alkoxyaryl with up to 18 carbon atoms respectively, wherein the total number of carbon atoms in $R^a$, $R^b$ and $R^c$ is at most 20; X is a common counter anion and is the same as in formula (I) and is preferably chloride. A cationic cellulose compound is marketed under the trade name Polymer JR of Amerchol and has the INCI name, polyquaternium-10. An additional cationic cellulose compound has the INCI name, polyquaternium-24, and is marketed by Amerchol under the trade name, Polymer LM-200, A suitable cationic guar derivative compound is marketed under the trade name Jaguar R and has the INCI name, guar hydroxypropyltrimonium chloride.

Chitosan, chitosan salts and chitosan derivative compounds are especially preferred as cation-active materials. The chitosan used in the composition of the invention is partially or completely deacetylated. Chitin is an economical and plentiful natural raw material available in the shell resides of crustaceans. The molecular weights of chitosans can vary over a wide range, for example from 20,000 to 5,000,000 g/mol. A low molecular weight chitosan is, for example, considered to be a chitosan with a molecular weight of from 30,000 to 70,000 g/mol. For the purpose of the present invention the molecular weight preferably is above 100,000 g/mol, especially preferably form 200,000 to 700,000 g/mol. The deacetylation degree amounts to from 10 to 99%, especially preferably form 60 to 99%.

A suitable chitosan is, for example, marketed under the trademark, FLONAC®, by Kyowa Oil & Fat, Japan. It has a molecular weight of 300,000 g/mol to 700,000 g/mol and is deacetylated from 70 to 80%. A preferred chitosan salt is chitosonium pyrrolidone carboxylate, which for example is marketed under the trade name Kytamer PC of Amerchol, USA. The chitosan obtained has a molecular weight of about 200,000 to 300,000 g/mol and is deacetylated up to 70 to 85%. Quaternary, alkylated or hydroxyalkylated derivative chitosan compounds, for example, the hydroxyethyl chitosan or hydroxybutyl chitosan, are suitable in the compositions according to the invention.

The chitosans or chitosan derivative compounds should be present in neutralized or partially neutralized form when used in the compositions of the invention. The neutralization degree for the chitosan or the chitosan derivative compounds is preferably at least 50%, especially preferably between 70 and 100%, relative to the number of free base groups. In principle, all cosmetically compatible inorganic or organic acids may be used as neutralization agent, for example formic acid, tartaric acid, malic acid, lactic acid, citric acid, pyrrolidone carboxylic acid, hydrochloric acid, among other. Pyrrolidone carboxylic acid is especially preferred as neutralization agent.

Those polymers which have sufficient alcohol solubility so that they are present in the composition according to the invention in completely dissolved form are especially preferred. The cationic charge density amounts to preferably from 1 to 7 meq/g.

Suitable cation-active silicone compounds have preferably either at least one amino group or at least one ammonium group. Suitable silicone polymers with amino groups are known as amodimethicone under the INCI nomenclature system. This compound is a polydimethylsiloxane with aminoalkyl substituent groups. The aminoalkyl groups can be those of the general formula (IV):

wherein
- $R^8$, $R^9$, $R^{14}$ and $R^{15}$, independently of each other, are equal or different and each represent $C_1$- to $C_{10}$-alkyl, phenyl, hydroxy, hydrogen, $C_1$- to $C_{10}$-alkoxy or acetoxy, preferably $C_1$- to $C_4$-alkyl, especially preferably methyl;
- $R^{10}$ and $R^{16}$ are the same or different and, independently of each other, represent $-(CH_2)_a-NH_2$ with a=1 to 6, $C_1$- to $C_{10}$-alkyl, phenyl, hydroxy, hydrogen, $C_1$- to $C_{10}$-alkoxy or acetoxy, preferably $C_1$- to $C_4$-alkyl, especially preferably methyl;
- $R^{11}$, $R^{12}$ and $R^{13}$ are the same or different and independently of each other each represent hydrogen, a $C_1$- to $C_{20}$-substituted hydrocarbon group with at least one O and/or N atom substituent and an $C_1$- to $C_{20}$- unsubstituted hydrocarbon group, preferably a $C_1$- to $C_{10}$-alkyl or phenyl group, especially preferably a $C_1$- to $C_4$-alkyl group, most preferably methyl;
- Q represents $-A-NR^{17}R^{18}$, or $-A-N^+R^{17}R^{18}R^{19}$, wherein A stands for a divalent $C_1$- to $C_{20}$-alkylene compound group, which can contain an O—, N— or OH substituent group, and $R^{17}$, $R^{18}$ and $R^{19}$, independently of each other, are equal or different and represent hydrogen, a $C_1$- to $C_{22}$-substituted hydrocarbon group, preferably a $C_1$- to $C_4$-alkyl or phenyl group;
- X represents a number between 1 and 10,000, preferably between 1 and 1000; and Y represents a number between 1 and 500, preferably between 1 and 50.

Preferably Q stand for $-(CH_2)_3-NH_2$, $-(CH_2)_3NHCH_2CH_2NH_2$, $-(CH_2)_3OCH_2-CHOHCH_2NH_2$ and $-(CH_2)_3N(CH_2CH_2OH)_2$, $-(CH_2)_3-NH_3^+$ and $-(CH_2)_3OCH_2CHOH-CH_2N^+(CH_3)_2R^{20}$, wherein $R^{20}$ is a $C_1$- to $C_{22}$-alkyl residue.

The molecular weight of the amino-silicones is between 500 and 100,000 g/mol. The amine content (meq/g) is preferably in a range of from 0.05 to 2.3, especially preferably from 0.1 to 0.5.

Suitable silicone polymers with two terminal quaternary ammonium groups are known under the INCI name Quaternium-80. The silicone polymers are dimethylsiloxanes with two terminal aminoalkyl groups. The quaternary aminosilicones that are suitable have the following general formula (V):

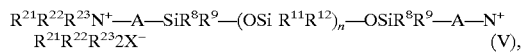

wherein A has the same significance as in the above formula (IV) and is preferably $-(CH_2)_3OCH_2CHOH-CH_2N^+(CH_3)_2R^{20}$, wherein $R^{20}$ is a $C_1$- to $C_{22}$-alkyl residue, which can have an OH group substitutent;
- wherein $R^8$, $R^9$, $R^{11}$ and $R^{12}$ have the same significance as above in formula (IV) and are preferably methyl groups;
- wherein $R^{21}$, $R^{22}$ and $R^{23}$, independently of each other, each represent a $C_1$- to $C_{22}$-alkyl residue, which can also contain hydroxy group substituents and wherein preferably at least one of the groups has at least 10 carbon atoms and the remaining groups have one to four carbon atoms; and
- n is a number from 0 to 200, preferably 10 to 100.

These diquaternary polydimethylsiloxanes are marketed under the trademark ABIL® QUAT 3270, 3272 and 3274 of Goldschmidt, Germany.

Further suitable cation-active hair-care compounds are cationically modified protein derivative compounds or cationically modified protein hydrolyzates and for example are known under the INCI name lauryldimonium hydroxylpropyl hydrolyzed wheat protein, lauryldimonium hydroxypropyl hydrolyzed caesin, lauryldimonium hydroxypropyl hydrolyzed collagen, lauryldimonium hydroxypropyl hydrolyzed keratin, lauryldimonium hydroxypropyl hydrolyzed silk, lauryldimonium hydroxypropyl hydrolyzed soy protein or hydroxypropyltrimonium hydrolyzed wheat, hydroxypropyltrimonium hydrolyzed caesin, hydroypropyltrimonium hydrolyzed collagen, hydroxypropyltrimonium hydrolyzed keratin, hydroxypropyltrimonium hydrolyzed rice bran protein, hydroxypropyltrimonium hydrolyzed silk, hydroxypropyltrimonium hydrolyzed soy protein, hydroxypropyltrimonium hydroxlyzed vegetable protein.

Suitable cationic derivatized protein hydrolyzates are mixed substances that can be obtained, for example, by reaction of alkaline, acidic or enzymatically hydrolyzed proteins with glycidyltrialkyl ammonium salts or 3-halo-2-hydroxypropyltrialkyl ammonium salts. Proteins, which act as starting materials for the protein hydrolyzates, can be of both vegetable or animal origin. Conventional stating materials are, for example, keratin, collagen, elastin, soy protein, rice protein, milk protein, wheat protein, silk protein or almond protein. A mixed material is produced by hydrolysis with a mixed molecular weight of from about 100 to about 50,000. Usually the average molecular weight is in a range of from about 500 to about 1000. Preferably the cationic derivatized protein hydrolyzates contain one or two long $C_8$- to $C_{22}$-alkyl chains and two or one short $C_1$- to $C_4$-alkyl groups. Compounds with the long alkyl chains are preferred.

In a preferred embodiment the composition according to the invention contains at least one nonionic surfactant. The nonionic surfactant is contained preferably in an amount of from 0.01 to 15, especially preferably from 0.05 to 5, percent by weight.

Ethoxylated surfactants having between 1 and 1000 ethylene oxide units are preferred. However ethoxylated surfactants having between 1 and 300 ethylene oxide units are especially preferred and those having from 1 to 15 ethylene oxide units are most preferred. Fatty alcohol ethoxylates, fatty amine ethoxylates, fatty acid alkanol amide ethoxylates and fatty acid ester ethoxylates with 1 to 15 ethylene oxide units are especially preferred. For example, the suitable fatty alcohol ethoxylates include ethoxylated lauryl alcohol, tetradecyl alcohol, cetyl alcohol, oleyl alcohol or stearyl alcohol. These ethoxylated fatty alcohols can be used alone or in a mixture with each other. Also ethoxylated lanolin or ethoxylated lanolin is suitable. The ethoxylated fatty alcohols, which are marketed under the trademark DEHYDOL® of Henkel or under the trademakr BRIJ® of ICI surfactants, are suitable for use in the hair treatment composition according to the invention.

Preferred fatty acid ester ethoxylates include, above all, diglyceride ethoxylates, which are marketed by ICI surfactants under the trademark ARLATONE® G; ethoxylated castor oil ethoxylated with 25 ethylene oxide units designated by the INCI name, PEG-25 hydrogenated castor oil, which is marketed under the trademark CREMOPHOR® EL by BASF; ethoxylated castor oil with 35 ethylene oxide units designated by the INCI name PEG-35 castor oil, which is marketed by BASF under the trademark CREMOPHOR® RH 410, ethoxylated with 40 ethylene oxide units; hydrogenated castor oil with the INCI name PEG-40 hydrogenated castor oil, and the raw materials marketed by Witco Surfactants under the trademark REWODERM® LI.

The nonionic surfactants for the cosmetic preparation according to the invention can also include ethoxylated fatty acid sugar esters, especially ethoxylated sorbitan fatty acid ester, but also non-ethoxylated surfactants, such as the fatty acid sugar esters, which are sold by the firm ICI Surfactants under the trademark TWEEN® and ARLACEL® as well as the alkylpolyglycosides, which are sold by the Henkel under the trademark PLANTACARE® OR PLANTAREN® or under the trademark ORAMIX® by Seppic.

Generally it may be stated that nonionic surfactants are suitable for the hair treatment composition when they have an HLB value of at most 20, preferably from 5 to 18. A mixture of two surfactants in which one surfactant has an average HLB value of about 8 to 11 and the other has a higher HLB value of about 14 to 17 is especially preferred. For example, a mixture of tetraethoxylauryl ether (HLB 9.5) and polysorbate-40 (HLB value 15.6) is suitable.

In additional preferred embodiment the composition according to the invention contains from 0.01 to 15 percent by weight, preferably from 0.5 to 10 percent by weight of at least one synthetic or natural nonionic film-forming polymer. Those polymers are especially preferred, which have a sufficient solubility in alcohol or water/alcohol mixtures, so that they are completely dissolved.

The film-forming polymers are defined, according to the present invention, as those polymers, which are in a position to deposit a polymer film on the hair when used in an 0.01 to 5% by weight aqueous, alcoholic or aqueous-alcoholic is solution.

Suitable synthetic, nonionic film-forming hair-fixing polymers are homo- or copolymers, which are built up from at least one of the following monomers: vinyl pyrrolidone, vinyl caprolcactam, vinyl esters, such as vinyl acetate, vinyl alcohol, acrylamide methacrylamide, alkyl- and dialkylacrylamides, alkyl- and dialkylmetharcylamides, alkylacrylates, alkylmethacrylates, propylene glycol or ethylene glycol. The alkyl groups in these monomers preferably have from one to seven carbon atoms, especially preferably from one to three carbon atoms.

Suitable nonionic film-forming hair fixing polymers are, for example, homopolymers of vinylcaprolactam, of vinyl pyrrolidone or of N-vinylformamide. Additional suitable synthetic film-forming, nonionic, hair-fixing polymers are, for example, copolymerizates of vinyl pyrrolidone and vinyl acetate, terpolymers of vinyl pyrrolidone, vinyl acetate and vinyl propionate, polyacrylamides, which are sold, for example, under the trademark AKYPOMINE® P 191 of CHEM-Y, Emmerich, or SEPIGEL® 305 of Seppic; polyvinyl alcohols, which are sold for example under the trademark ELVANOL® of Dupont or VINOL® 523/540 of Air Products and polyethylene glycol/polypropylene glycol copolymers, which are sold, for example, under the trademark UCON® of Union Carbide. Polyvinyl pyrrolidone and polyvinyl pyrrolidone/vinyl acetate copolymers are especially preferred.

Suitable natural film-forming polymers are, for example, cellulose derivative compounds, e.g. hydroxypropyl cellulose with a molecular weight of 30,000 to 50,000 g/mol, which is marketed, for example, under the trademark NISSO SL® of Lehmann & Voss, Hamburg, Germany.

The composition according to the invention is provided preferably in an aqueous, an alcoholic or in an aqueous-alcoholic medium with preferably at least ten percent by weight water. The lower alcohols, with 1 to 4 carbon atoms, especially ethanol and isopropanol, which are normally used for cosmetic purposes, are especially suitable as the alcohols. The composition according to the invention can have a pH of from 2.0 to 9.5. A pH in a range of from 2.5 to 8 is especially preferred.

Organic solvents with a boiling point under 400° C., or mixtures of these solvents, can be present in the composition according to the invention as additional co-solvents. The additional co-solvents can be present in an amount of from 0.1 to 15 percent by weight, preferably from 1 to 10 percent by weight. Branched or unbranched hydrocarbons such as pentane, hexane and isopentane, and cyclic hydrocarbons, such as cyclopentane and cyclohexane, are especially suitable as the additional co-solvents. Glycerol and propylene glycol in amounts up to 30 percent by weight are especially preferred as the water-soluble solvents.

Furthermore the composition according to the invention can contain conventional additive ingredients usually used for hair treatment composition, for example wetting agents and emulsifiers from the classes of anionic or amphoteric surface active substances, such as fatty alcohol sulfates, alkyl-benzene sulfonates, alkyltrimethyl ammonium salts, alkyl betaines, in an amount of from 0.1 to 15 percent by weight; moisturizing agents; perfume oils, in an amount of 0.1 to 0.5 percent by weight; turbidity-inducing agents, for example ethylene glycol distearates, in an amount of about 0.2 to 5.0 percent by weight; pearlescence-imparting agents, such as a mixture of fatty acid monoalkylolamides and ethylene glycol distearate, in an amount of about 1.0 to 10 percent by weight; bactericides and fungicides, for example 2,4,4-trichloro-2-hydroxydiphenyl ether or methyl chlorisothiazolione, in an amount of from 0.01 to 1.0 percent by weight; thickeners, such as coconut oil fatty acid diethanol amides, in an amount of from about 0.2 to 3.0 percent by weight; buffer substances, such as sodium citrate or sodium phosphate, in an amount of from 0.1 to 1.0 percent by weight; dye substances, such as fluorescein sodium salt, in an amount of from about 0.1 to 1.0 percent by weight; care substances, such as plant and vegetable extracts, protein and silk hydrolyzates, lanolin derivative compounds, in an amount of from 0.1 to 5 percent by weight; physiologically compatible silicone derivative compounds, such as volatile or non-volatile silicones or high molecular weight siloxane polymers, in an amount of from 0.05 to 20 percent by weight; light-protective ingredients, antioxidants, radical-trapping agents, anti-flaking agents, in an amount of from about 0.01 to 2 percent by weight; direct-dyeing dye compounds, hair dye precursor compounds which are developed oxidatively, oxidizing agents, reducing agents, fatty alcohols, luster-imparting substances, vitamins, softeners, combability improving substances, defatting agents and antifoaming agents.

The composition according to the invention can be provided in different forms, for example as a lotion, a non-aerosol spray lotion, which is sprayed by means of a mechanical device, an aerosol-foam or non-aerosol foam, which is present in combination with a suitable mechanical device for foaming the preparation. Also it can be provided as a lotion thickened with a suitable thickener.

When the composition according to the invention is present in the form of a hair-fixing hair lotion, it can be a non-viscose solution, dispersion or emulsion with a content of at least 10 percent by weight, preferably 20 to 95 percent by weight of a cosmetically compatible alcohol. As alcohol lower alcohols with one to four carbon atoms commonly used for cosmetic purposes, such as ethanol and isopropanol, are especially preferred for use in this embodiment of the composition according to the invention. The lotion according to the invention is packaged in a portion bottle and can be applied directly to the hair. In order to obtain a volume effect directly on the hair roots, the package can be equipped with a nozzle, by means of which a direct application on the hair roots is possible.

A non-aerosol spray lotion is an especially preferred form of the composition according to the invention. This embodiment of the composition according to the invention is sprayed with the help of a suitable mechanically operated spraying device. The "mechanical spraying devices" are defined, for the purposes of the present invention, as those devices, which permit spraying of a liquid without use of a propellant. A spray pump, for example, is a suitable mechanical spraying device. Another suitable mechanical spraying device comprises an elastic container provided with a spray valve, in which the cosmetic composition according to the invention is filled under pressure so that the elastic container stretches or expands. The cosmetic composition contained in the container is dispensed from it when the spray valve is opened because of contraction of the elastic container.

When the composition according to the invention is present in the form of hair-fixing foam (mousse), it contains at least one known form-generating substance, suitable for this purpose. The composition is foamed with or without the aid of a propellant gas or chemical propellant and worked into the hair as a foam and is left on the hair without rinsing off. The hair foam according to the invention has a chemical propellant as an additional ingredient and/or a mechanical apparatus for foaming the composition. A "foaming apparatus" is defined, for the purposes of the present invention, as a device that permits foaming of the liquid with or without use of a propellant. A suitable mechanical foaming apparatus, for example, can be a conventional pump foaming device or an aerosol foam head.

In an especially preferred embodiment the composition according to the invention can be in the form of an aqueous, alcoholic or aqueous-alcoholic non-aerosol spray lotion in combination with a suitable mechanical device for spraying or in the form of an aqueous, alcoholic or aqueous-alcoholic lotion comprising:

(A) from 0.01 to 20, preferably from 0.1 to 5, percent by weight, of at least one terpolymer of vinyl pyrrolidone, vinyl caprolactam and a basic acrylamide monomer;

(B) from 0.01 to 10, preferably from 0.05 to 5, percent by weight of at least one additional cationic hair-care polymer;

(C) from 0.01 to 15, preferably from 0.5 to 10, percent by weight of at least one film-forming, nonionic polymer, and (D) from 0.01 to 10, preferably from 0.05 to 5, percent by weight of at least one cationic surfactant. The amounts of ingredients (A) to (D) are preferably adjusted so that a clear solution results.

The cosmetic composition according to the invention is applied to moistened hand-towel dried hair in a sufficient amount to produce a volumizing effect. Subsequently the hairstyle can be formed or the hair can be set in the usual manner and finally then dried. It is also possible to use the composition directly on the dried hair to refresh the volumizing effect.

The following examples should illustrated the subject matter of the invention.

EXAMPLES

Example 1

Aerosol Foam-fixing Composition

|  | 1A | 1B |
| --- | --- | --- |
| Polyquaternium-11 | — | 1.8 g |
| Vinylcaprolactam/PVP/DMAPA copolymer | 1.8 g | — |
| Cetyltrimethyl ammonium chloride | 0.1 g | 0.1 g |
| Laureth-4 | 0.18 g | 0.18 g |
| Perfume | 0.2 g | 0.2 g |
| Ethanol | 8.9 g | 8.9 g |
| Water | To 100 g | To 100 g |

The effective ingredient mixture was filled in an aerosol can with a foam valve in a ratio of 95:5 with propane/butane 5.0 as propellant.

One half of the hair of a test person was treated with the composition according to the invention, composition 1A, and the other half of the test person's hair was treated with the composition 1B that is not of the invention. Both halves of the treated hair were judged qualitatively by hairstyle professionals. The following results were obtained:

Comparing 1A to 1B

The feel of the hair treated with composition 1A of the invention was better than that produced by composition 1B for both wet and dry hair. The hair treated with composition 1A was better put in a hairstyle or set than that treated with composition 1B. Less dust or flecks of polymer substance were observed on the dried hair treated with the composition 1A.

Example 2

Pump Spray Lotion

|  | 1A | 1B |
|---|---|---|
| Polyvinyl pyrrolidone/vinyl acetate copolymer | — | 2.5 g |
| Vinylcaprolactam/PVP/DMAPA copolymer | 1.5 g | — |
| Cetyltrimethylammonium chloride | 0.2 g | 0.2 g |
| PEG-40 hydrogenated castor oil | 0.2 g | 0.2 g |
| Perfume | 0.25 g | 0.25 g |
| Ethanol | 27 g | 27 g |
| Water | To 100 g | To 100 g |

One half of the hair of a test person was treated with the composition according to the invention, composition 2A, and the other half of the test person's hair was treated with the composition 2B that is not of the invention. Both halves of the treated hair were judged qualitatively by hairstyle professionals. The following results were obtained:

Comparing 2A to 2B

In spite of reduced amounts of polymer the test preparation 2A according to the invention produced a stronger fixing effect and also preparation 2A provided better spray formation.

Example 3

Pump Foam-fixing Composition

|  | 3A | 3B | 3C |
|---|---|---|---|
| Polyvinyl pyrrolidone (K80) | — | — | 1.4 g |
| Vinylcaprolactam/PVP/DMAPA copolymer | 1.4 g | 0.9 g | — |
| Cocamidopropyl hydroxysultaine | 0.6 g | 0.6 g | 0.6 g |
| Cetyltrimonium chloride | 0.25 g | 0.25 g | 0.25 g |
| Betaine | 0.1 g | 0.1 g | 0.1 g |
| Citric acid | 0.1 g | 0.1 g | 0.1 g |
| Perfume | 0.15 g | 0.15 g | 0.15 g |
| Ethanol | 2.5 g | 2.5 g | 2.5 g |
| Water | To 100 g | To 100 g | To 100 g |

One half of the hair of a respective test person was treated with either composition 3A or 3B according to the invention and the other half of that test person's hair was treated with the composition 3C that is not of the invention. Both halves of the treated hair were judged qualitatively by hairstyle professionals. The following results were obtained:

Comparing 3A to 3C

Comparative amounts of the polymer composition provided more hold in the case of the preparation 3A according to the invention. The elasticity of the treated hair was greater with reduced load and a natural feel in the case of the preparation 3A according to the invention.

Comparing 3B with 3C

The same fixing effect was obtained with a smaller amount of composition 3B than that of 3C. Less visible residue was observed on the dried hair for composition 3B than composition 3C.

Example 4

Aerosol Foam-fixing Composition

| Vinylcaprolactam/PVP/DMAPA copolymer | 1.20 g |
|---|---|
| Polyquaternium-11 | 0.80 g |
| Betaine | 0.15 g |
| PEG 25 PABA | 0.50 g |
| Cetyltrimonium chloride | 0.07 g |
| Perfume | 0.15 g |
| Ethanol | 8.9 g |
| Water | To 100 g |

The effective ingredient mixture was filled in an aerosol can with a foam valve in a ratio of 95:5 with propane/butane 5.0 as propellant.

Example 5

Pump Spray Lotion

| Vinylcaprolactam/PVP/DMAPA copolymer | 1.00 g |
|---|---|
| Polyquaternium-16 | 0.20 g |
| Chitosan | 0.40 g |
| PVP/VA copolymer | 2.50 g |
| Formic acid | 0.12 g |
| Cetrimonium phosphate | 0.15 g |
| Laureth-4 | 0.10 g |
| Perfume | 0.10 g |
| Ethanol | 33 g |
| Water | To 100 g |

The hair treated with the spray lotion had a volumizing effect that holds over an entire day with good fixing and good stylability.

Example 6

Pump Foam-fixing Composition

| Vinylcaprolactam/PVP/DMAPA copolymer | 1.1 g |
|---|---|
| Polyquaternium-11 | 0.4 g |
| Cocamidopropyl hydroxysultaine | 0.6 g |
| Citric acid | 0.1 g |
| Betaine | 0.1 g |
| Perfume | 0.1 g |
| Ethanol | 8.9 g |
| Water | To 100 g |

Unless otherwise stated all percentages are percentages by weight.

The disclosure in German Patent Application 199 37 386.8-41 of Aug. 7, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in volume-imparting hair treatment compositions, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A volume-imparting hair treatment composition comprising
   from 0.1 to 20 percent by weight of at least one terpolymer made from vinyl pyrrolidone, vinyl caprolactam and a basic acrylamide monomer, and
   from 0.05 to 10 percent by weight of at least one hair-care material with at least one cationic group;
   wherein said at least one hair-care material is selected from the group consisting of cationic surfactant compounds, polymers with cationic or cationizable groups, silicone compounds with cationic or cationizable groups, cationic derivatized proteins, cationic derivatized protein hydrolyzates and betaines.

2. The hair treatment composition as defined in claim 1, wherein said basic acrylamide monomer is selected from the group consisting of dialkylaminoalkylmethacrylamides having alkyl groups with 1 to 4 carbon atoms and dialkylaminoalkylacrylamides having alkyl groups with 1 to 4 carbon atoms.

3. The hair treatment composition as defined in claim 1, wherein said cationic surfactant compounds are surface-active compounds of formula I:

$$N^{(+)}R^1R^2R^3R^4 X^{(-)} \qquad (I),$$

wherein $R^1$ to $R^4$ each represent, independently of each other, an aliphatic group, an aromatic group, an alkoxy group, an polyoxyalkylene group, an alkylamido group, a hydroxyalkyl group, an aryl group or an alkaryl group with 1 to 22 carbon atoms, and $X^{(-)}$ represents an anion.

4. The composition as defined in claim 1, wherein said polymers with the cationic or cationizable groups consist of methyl vinyl imidazolium chloride/vinyl pyrrolidone copolymers, quaternarized vinyl pyrrolidone/dimethylamino-ethylmethacrylate copolymers, cationic derivatized polysaccharides, chitosan, chitosan salts and chitosan derivative compounds.

5. The composition as defined in claim 1, further comprising at least one nonionic film-forming polymer.

6. The composition as defined in claim 5, wherein said at least one nonionic film-forming polymer is selected from the group consisting of polyvinyl pyrrolidone and polyvinyl pyrrolidone/vinyl acetate copolymers.

7. The composition as defined in claim 1, in the form of a lotion, a non-aerosol spray lotion for spray application with a mechanical spraying device, an aerosol foam for spray application with the help of a propellant or a non-aerosol foam for spray application by means of a mechanical spraying device.

8. A volume-imparting hair treatment composition in the form of an aqueous, alcoholic, aqueous-alcoholic lotion or non-aerosol spray lotion, said hair treatment composition comprising:
   from 0.1 to 20 percent by weight of at least one terpolymer of vinyl pyrrolidone, vinyl caprolactam and a basic acrylamide monomer;
   from 0.05 to 10 percent by weight of at least one cationic hair-care polymer;
   from 0.5 to 15 percent by weight of at least one film-forming, nonionic polymer; and
   from 0.05 to 10 percent by weight of at least one cationic surfactant.

9. The hair treatment composition as defined in claim 8, wherein said basic acrylamide monomer is selected from the group consisting of dialkylaminoalkylmethacrylamides with alkyl groups having 1 to 4 carbon atoms and dialkylaminoalkylacrylamides with alkyl groups having 1 to 4 carbon atoms.

10. The hair treatment composition as defined in claim 8, wherein said at least one cationic hair-care polymer is selected from the group consisting of methyl vinyl imidazolium chloride/vinyl pyrrolidone copolymers, quaternarized vinyl pyrrolidone/dimethylaminoethyl methacrylate copolymers, cationic derivatized polysaccharides, chitosan, chitosan salts and chitosan derivative compounds.

11. The hair treatment composition as defined in claim 8, wherein said nonionic polymer is selected from the group consisting of polyvinyl pyrrolidone and polyvinylpyrrolidone/vinyl acetate copolymers.

12. The hair treatment composition as defined in claim 8, wherein said at least one cationic surfactant compound is selected from the group consisting of compounds of formula I:

$$N^{(+)}R^1R^2R^3R^4 X^{(-)} \qquad (I),$$

wherein $R^1$ to $R^4$ each represent, independently of each other, an aliphatic group, an aromatic group, an alkoxy group, an polyoxyalkylene group, an alkylamido group, a hydroxyalkyl group, an aryl group or an alkaryl group with 1 to 22 carbon atoms, and $X^{(-)}$ represents an anion.

* * * * *